(12) United States Patent
Chand et al.

(10) Patent No.: US 6,503,745 B1
(45) Date of Patent: Jan. 7, 2003

(54) CYCLOPENTANE AND CYCLOPENTENE COMPOUNDS AND USE FOR DETECTING INFLUENZA VIRUS

(75) Inventors: Pooran Chand, Birmingham, AL (US); Yarlagadda S. Babu, Birmingham, AL (US); Shanta Bantia, Birmingham, AL (US)

(73) Assignee: Biocryst Pharmaceuticals, Inc., Birmingham, AL (US)

( * ) Notice: Subject to any disclaimer, the term of this patent is extended or adjusted under 35 U.S.C. 154(b) by 0 days.

(21) Appl. No.: 09/831,140

(22) PCT Filed: Nov. 5, 1999

(86) PCT No.: PCT/US99/26054

§ 371 (c)(1), (2), (4) Date: Aug. 13, 2001

(87) PCT Pub. No.: WO00/28328

PCT Pub. Date: May 18, 2000

Related U.S. Application Data

(60) Provisional application No. 60/107,139, filed on Nov. 5, 1998, and provisional application No. 60/139,791, filed on Jun. 21, 1999.

(51) Int. Cl.$^7$ .................. C12N 9/14; C07D 235/02; C07C 69/74; C07C 61/06

(52) U.S. Cl. .................. 435/195; 548/303.7; 560/122; 562/504

(58) Field of Search .................. 435/195; 548/303.7; 560/122; 562/504

(56) References Cited

U.S. PATENT DOCUMENTS

| | | | |
|---|---|---|---|
| 4,426,391 A | 1/1984 | Alexander et al. | |
| 5,362,728 A | 11/1994 | Asberom et al. | 514/217 |
| 5,453,533 A | 9/1995 | Luo et al. | 560/142 |
| 5,602,277 A | 2/1997 | Babu et al. | 562/439 |
| 5,739,160 A | 4/1998 | Mittendorf et al. | 514/510 |
| 5,789,434 A | 8/1998 | Kluender et al. | 514/414 |
| 6,242,582 B1 * | 6/2001 | Reece et al. | 536/4.1 |

FOREIGN PATENT DOCUMENTS

| | | |
|---|---|---|
| EP | 0 130 119 A2 | 1/1985 |
| EP | 0 743 320 A2 | 11/1996 |
| JP | 49-185 | 1/1974 |
| JP | 59-163365 | 9/1984 |
| JP | 63-179835 | 7/1988 |
| JP | 05065255 | 3/1993 |
| WO | WO92/16541 | 10/1992 |
| WO | WO 97/47194 | * 12/1997 |
| WO | WO 98/34935 | 8/1998 |
| WO | WO 99/33781 | 7/1999 |
| WO | WO 99/54290 | 10/1999 |
| WO | WO 99/54299 | 10/1999 |

OTHER PUBLICATIONS

Aldrich catalog, p. 362, 1992–1993 edition.*
Rao et al, Synthesis of oxa–and thia–analogs of bicyclo [n.3.0] alkanes, Indian J. Chem., Sec. B (1987), 26B(10, 939–46, abstract.
Sakurai et al, Synthetic study of HIV–1 protease inhibitors, Pept. Chem. (1993), 31st, 185–8, abstract.
Allan et al, Synthesis of Analogues of GABA, XV Preparation and Resolution of Some Potent Cyclopentene and Cyclopentane Derivatives, Aust. J. Chem., 1986, 39, 855–864.
Collect. Czech. Chem. Commun. vol. 58 (1993) pp. 2159–2179.
Kogyo Kagaku Zashi vol. 60, No. 3 (1957) pp. 355–356.
Journal of Medical Chemistry, vol. 21, No. 3, pp. 245–248.
Tetrahedron vol. 51, No. 37, pp. 10259–10280 (1995).
Chem. Pharm. Bull. 38(12) pp. 3242–3248 (1990).
Chemical Abstracts, vol. 65 10460 c. (1966).
Chemical Abstracts, vol. 62 9031 d–e (1965).
Bundgaard, Hans. Design of prodrugs, Elsevier, 1985, pp. 3–5.
Chemical Abstracts, vol. 65 15301 c (1966).
Bergmeier et al., "Chirospecific Synthesis of (1S, 3R)—1–Amino–3–(hydroxymethyl) cyclopentane, a Precursor for Carbocyclic Nucleoside Synthesis. Intramolecular Aziridine Cyclizations", J. Org. Chem., 1993, No. 58, pps. 5019–5022.
Mohamed–Cherif Boucemma et al., "Magnetic Studies of the Structure and the Red Photolysis Reactions of 2–Chloro–2–Nitrosonobornane", J. Chem. Soc, Perkin Trans. 2 (1995), pp. 1381–1387.
Database CAPLUS on STN, Chem. Abstract (Columbus, OH, USA) AN 2001:12411, Abdel–Magid, et al. 'Process for preparing substituted cyclopentane derivatives and their crystalline structures' PCT Int. Appl. US16013 (2000).
Database CAPLUS on STN, Chem. Abstract (Columbus, OH, USA) AN 2000: 307903, Sorbera, et al. 'RWJ–270201: anti–influenza neuraminidase (sialidase) inhibitor' Drug Future (2000), 25 (3), pp. 249–251.
Database CAPLUS on STN, Chem. Abstract (Columbus, OH, USA) AN 2001:12400, Chand, et al. 'Preparation of substituted cyclopentane and cyclopentene compounds and certain intermediates' PCT Appl. US17685 (2000).
Database CAPLUS on STN, Chem. Abstract (Columbus, OH, USA) An 2000: 605951, Babu et al. 'Bcx–1812 (rwj–270201) :discovery of a novel highly potent orally active and selective influenza neuraminidase inhibitor through structure–based drug design' J. Me. Chem. v. 43, pp. 3482–3486 (2000).
Toshihiro Yamamoto et al, "Syntheses of Sialic Acid Isomers with Inhibitory Activity Against Neuraminidase", Tet. Lett., vol. 33 (1992), pp. 5791–5794.

* cited by examiner

Primary Examiner—James O. Wilson
Assistant Examiner—Leigh C. Maier
(74) Attorney, Agent, or Firm—Connolly Bove Lodge & Hutz LLP

(57) ABSTRACT

New cyclopentane and cyclopentene compounds are provided along with their use in method for detecting influenza virus.

39 Claims, No Drawings

CYCLOPENTANE AND CYCLOPENTENE
COMPOUNDS AND USE FOR DETECTING
INFLUENZA VIRUS

This application is a National Stage entry of PCT/US99/26054, filed Nov. 5, 1999. This application claims the benefit of provisional applications No. 60/107,139 filed Nov. 5, 1998 and No. 60/139,791, filed Jun. 21, 1999.

TECHNICAL FIELD

The present invention is concerned with a new group of cyclopentane and cyclopentene compounds and their use as diagnostic agents for detecting influenza A and B. The compounds of the present invention bind to influenza A and B neuraminidase. Moreover, these compounds possess functionality which allows them to be bound to a surface or to a detectable label.

The diagnostic method of the present invention depends upon the ability of the disclosed compounds to bind specifically to the active site of influenza virus neuraminidase, or functionalized derivatives of such compounds, as binding and/or detecting agents to identify influenza virus in clinical specimens. The term "neuraminidase binders" is used hereinafter to refer to these compounds and their functionalized derivatives. The method and compounds of the present invention can function either in the presence or the absence of compounds binding non-specifically to influenza virus neuraminidase.

BACKGROUND OF INVENTION

Influenza A and B viruses are major causes of acute respiratory disease, with an estimated 30–50 million infections annually in the United States alone. Influenza A has been responsible for major epidemics, such as the "Spanish flu" of 1919 which killed millions of people. Many viral and bacterial infections may exhibit symptoms similar to those of influenza. The rapid identification of respiratory viruses would enable physicians to use the most appropriate therapy early in the illness. For example, an early and accurate diagnosis would allow decisions regarding the use of anti-bacterial therapy and hospitalization of children and the elderly.

Laboratory tests for the identification of viruses in clinical material are widely used, and a variety of different detection methodology is available. The textbook, *Laboratory Diagnosis of Viral Infections*, Marcel Dekker, 1992, Ed. E. H. Lennette, generally discusses methods which are used for a wide range of viruses, including influenza virus.

A number of tests are available for the diagnosis of influenza A and B. The traditional method of identifying influenza viruses has been the use of cell culture, which is highly sensitive and specific. Unfortunately, the time required for culture, isolation and identification of influenza virus can range between 2 and 10 days, thus making it virtually useless in guiding the physician to an appropriate therapy. Since influenza virus infection is normally self-limited, diagnosis must be rapid if therapy is to be effective. In other words, such cell culture methods are normally only of value in providing retrospective epidemiological information.

In addition to the cell culture methods for detecting influenza, there have recently become available a few rapid direct tests, which are specific for influenza A. Thus, a monoclonal immunofluorescence assay (IFA) has been reported (Spada, B. et al., *J. Virol. Methods,* 1991, 33: 305) and at least one enzyme immunoassay (EIA) is available (Ryan-Poirier, K. A. et al., *J. Clin. Microbiol.,* 1992, 30: 1072). A number of comparisons of these rapid detection methods for influenza A have been reported; see for example Leonardi, G. P. et al., *J. Clin. Microbiol.,* 1994, 32: 70, who recommended that direct specimen testing be used together with culture isolation, so as to permit both identification of the virus in time to institute therapy and infection control measures, and to monitor the antigenic constitution of influenza strains prevalent in the community for epidemiological purposes. The IFA method is reported to be labor-intensive, and requires considerable technical expertise, with the results often being difficult to interpret. On the other hand, the EIA method (Directigen FLU-A; Becton Dickinson Microbiology Systems) give a high level of false-positive results, and it has been recommended that this assay be used in laboratories only in addition to or as a substitute for direct immunofluorescence tests (Waner, J. L. et al., *J. Clin. Microbiol.,* 1991, 29: 479).

As well as the problems mentioned above with the available rapid assays for influenza, there are other fundamental deficiencies in some of these methods. Firstly, none of the available assays can detect influenza B, which means that even a negative test result would leave the physician uncertain about the type of therapy that should be used. Secondly, if a rapid immunoassay method depends on the use of antibodies to one of the influenza A proteins, there may be a serious problem in detecting new strains of the virus which have undergone a drift or shift in the structure of the antigenic proteins. Influenza A is notorious for its propensity to undergo such changes.

Neuraminidase is one of the key proteins present on the surface of the influenza virus, and it plays an important role in the ability of the virus to infect human cells. It has long been thought that agents which bind to the neuraminidase enzyme might prevent invention by influenza, and much effort has gone into seeking such binders. While many compounds have shown in vitro activity against influenza neuraminidase, only recently has it been established that it is possible to achieve protection from influenza infection in vivo by the use of a powerful neuraminidase binder which binds to the active site of the enzyme (see von Itzstein, M. et al., *Nature,* 1993, 363: 418 and International Patent Applications No. WO 92/06691 and WO 91/16320). In particular, it has been found that 2,3-didehydro-2,4-dideoxy-4-guanidinyl-N-acetylneuraminic acid (Compound I, designated GG167) is a potent binder of influenza neuraminidase, and also shows potent in vivo antiviral activity in animals (Ryan, D. M. et al., *Antimicrobiol Agents and Chemotherapy,* 1994, 38: 2270) and in human volunteers (Hayden, F. G. et al., *J. American Medical Assoc.,* 1996, 275: 295).

Compound (I)

GG167

More recently, it has been found that certain substituted cyclohexene derivatives of sialic acid are also potent binders of influenza virus neuraminidase (Kim, C. U. et al., *J. Amer.*

Chem. Soc., 1997, 119: 681), and specifically the compound (3R,4R,5S)-4-acetamido-5-amino-3-(1-ethylpropoxy)-1-cyclohexene-1-carboxylic acid (GS 4071).

It is the purpose of the present invention to provide a simple and sensitive means for detecting influenza viruses.

SUMMARY OF INVENTION

The present invention is concerned with cyclopentane and cyclopentene compounds represented by the following formulae:

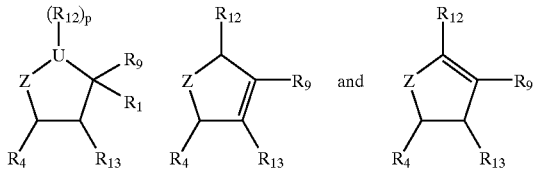

wherein:

U is CH, O or S;

Z is $—C(R_2)R_3)$, $—CH—N(R_2)(R_3)$, $C(R_3)[(CH_2)nR_2]$, or $CH—C(R_3)(CH_2)nR_2$;

$R_1$ is H, $(CH_2)nOH$, $(CH_2)nNH_2$, $(CH_2)nNR_{10}R_{11}$, $(CH_2)nOR_{11}$, $(CH_2)nSR_{11}$, or $(CH_2)n$ halogen;

$R_9$ is $(CH_2)nCO_2H$, $(CH_2)nSO_3H$, $(CH_2)nPO_3H_2$, $(CH_2)nNO_2$, esters thereof, or salts thereof;

$R_2$ is H, $NHC(O)R_5$, $NHC(S)R_5$, $NHSO_2R_5$, $C(O)NHR_5$, $SO_2NHR_5$, $CH_2S(O)R_5$, or $CH_2SO_2R_5$;

$R_3$ is H, $(CH_2)nCO_2R_{10}$, $(CH_2)mOR_{10}$, $C(O)N(R_{10})m$, $(CH_2)nN(R_{10})m$, $CH(R_{10})m$, $(CH_2)n(R_{10})m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{11})CH_2NHR_{10}$, $CH(OR_{10})CH(OR_{10})CH_2NHR_{10}$, $C(=NR_{10})N(R_{10})m$, $NHR_{10}$, $NHC(=NR_{10})N(R_{10})m$, $(CH_2)m-X—W—Y$, $CH_2CH(X—W—Y)CH_2OR_{10}$, $CH(X—W—Y)CH(OR_{10})CH_2OR_{10}$, $CH(X—W—Y)CH_2(OR_{10})$, $CH(OR_{10})CH(X—W—Y)CH_2OR_{11}$, $CH(OR_{10})CH_2(X—W—Y)$, $CH_2CH(X—W—Y)CH_2NHR_{10}$, $CH(X—W—Y)CH(OR_{11})CH_2NHR_{10}$, $CH(X—W—Y)CH_2(NHR_{10})$, $CH(OR_{10})CH(X—W—Y)CH_2NHR_{11}$, or $CH(NHR_{10})CH_2(X—W—Y)$;

$R_4$ is H, $(CH_2)nOH$, $(CH_2)nNR_{10}R_{11}$, $(CH_2)nNH_2$, $(CH_2)nC(=NH)(NH_2)$, $(CH_2)nNHC(=NR_{11})NH_2$, $(CH_2)nNHC(=NR_7)NH_2$, $(CH_2)nCN$, $(CH_2)nN_3$, $C(=NH)NH_2$, $C(NR_7)NH_2$, or $C(NR_{11})NH_2$;

$R_5$ is H, lower alkyl, branched chain alkyl, cyclic alkyl, halogen substituted alkyl, aryl, substituted aryl, or $CF_3$;

$R_7$ is H, $(CH_2)nOH$, $(CH_2)nCN$, $(CH_2)nNH_2$, or $(CH_2)nNO_2$;

$R_{10}$ is H, lower alkyl, lower alkylene, branched alkyl, cyclic alkyl, $(CH_2)n$ aromatic, $(CH_2)n$ substituted aromatic, or when m is 2 both $R_{10}$ groups can also be interconnected to form an N substituted heterocyclic ring, or other 5 or 6 membered heterocyclic ring;

$R_{11}$ is lower alkyl, branched alkyl, $(CH_2)m$ aromatic, or $C(O)OR_{10}$;

$R_{12}$ and $R_{13}$ is H, $(CH_2)nOH$, $(CH_2)nNH_2$, $(CH_2)nNR_{10}R_{11}$, $(CH_2)nOR_{11}$, $(CH_2)nF$, $(CH_2)nOC(O)R_{11}$, $(CH_2)nNHC(O)R_{11}$, or $X—W—Y$;

m is 1 or 2;

n is 0–4;

p is 0 or 1;

X is O, S, $CH_2$, or NH;

W is a spacer group made up of a chain of 4 to 100 atoms, and optionally also comprising of substituted carbon and/or nitrogen atoms and optionally including oxygen or sulphur atoms;

Y is OH, SH, $NH_2$, $CH=O$, $CH=CH_2$, $CO_2H$, $CONHNH_2$, or NH-biotinyl, or a protected form of one of these end functionalities.

It has been found according to the present invention that the compounds of the present invention can be used to detect influenza virus by selectively binding the influenza virus and by being able to attach to a surface or to a detectable linking group. Therefore, another aspect of the present invention relates to a method for detecting influenza virus. The method comprises the step of exposing a sample suspected to comprise the influenza virus to at least one of the above-disclosed compounds.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The cyclopentane and cyclopentene compounds of the present invention are represented by the following formulae:

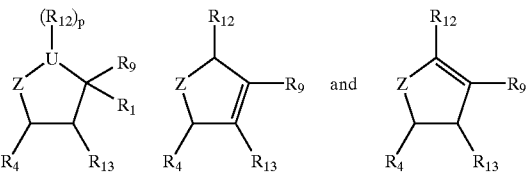

wherein:

U is CH, O or S;

Z is $—C(R_2)R_3)$, $—CH—N(R_2)(R_3)$, $C(R_3)[(CH_2)nR_2]$, or $CH—C(R_3)(CH_2)nR_2$;

$R_1$ is H, $(CH_2)nOH$, $(CH_2)nNH_2$, $(CH_2)nNR_{10}R_{11}$, $(CH_2)nOR_{11}$, $(CH_2)nSR_{11}$, or $(CH_2)n$ halogen;

$R_9$ is $(CH_2)nCO_2H$, $(CH_2)nSO_3H$, $(CH_2)nPO_3H_2$, $(CH_2)nNO_2$, esters thereof, or salts thereof;

$R_2$ is H, $NHC(O)R_5$, $NHC(S)R_5$, $NHSO_2R_5$, $C(O)NHR_5$, $SO_2NHR_5$, $CH_2S(O)R_5$, or $CH_2SO_2R_5$;

$R_3$ is H, $(CH_2)nCO_2R_{10}$, $(CH_2)mOR_{10}$, $C(O)N(R_{10})m$, $(CH_2)nN(R_{10})m$, $CH(R_{10})m$, $(CH_2)n(R_{10})m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{11})CH_2NHR_{10}$, $CH(OR_{10})CH(OR_{10})CH_2NHR_{10}$, $C(=NR_{10})N(R_{10})m$, $NHR_{10}$, $NHC(=NR_{10})N(R_{10})m$, $(CH_2)m-X—W—Y$, $CH_2CH(X—W—Y)CH_2OR_{10}$, $CH(X—W—Y)CH(OR_{10})CH_2OR_{10}$, $CH(X—W—Y)CH_2(OR_{10})$, $CH(OR_{10})CH(X—W—Y)OH_2CR_{10}$, $CH(OR_{10})CH_2(X—W—Y)$, $CH_2CH(X—W—Y)CH_2NHR_{10}$, $CH(X—W—Y)CH(OR_{10})CH_2NHR_{10}$, $CH(X—W—Y)CH_2(NHR_{10})$, $CH(OR_{10})CH(X—W—Y)CH_2NHR_{10}$, or $CH(NHR_{10})CH_2(X—W—Y)$;

$R_4$ is H, $(CH_2)nOH$, $(CH_2)nNR_{10}R_{11}$, $(CH_2)nNH_2$, $(CH_2)nC(=NH)(NH_2)$, $(CH_2)nNHC(=NR_{11})NH_2$, $(CH_2)$ nNHC(=NR$_7$)NH$_2$, (CH$_2$)nCN, (CH$_2$)nN$_3$, C(=NH)NH$_2$, C(NR$_7$)NH$_2$, or C(NR$_{11}$)NH$_2$;

R$_5$ is H, lower alkyl, branched chain alkyl, cyclic alkyl, halogen substituted alkyl, aryl, substituted aryl, or CF$_3$;

R$_7$ is H, (CH$_2$)nOH, (CH$_2$)nCN, (CH$_2$)nNH$_2$, or (CH$_2$)nNO$_2$;

R$_{10}$ is H, lower alkyl, lower alkylene, branched alkyl, cyclic alkyl, (CH$_2$)n aromatic, (CH$_2$)n substituted aromatic, or when m is 2 both R$_{10}$ groups can also be interconnected to form an N substituted heterocyclic ring, or other 5 or 6 membered heterocyclic ring;

R$_{11}$ is lower alkyl, branched alkyl, (CH$_2$)m aromatic, or C(O)OR$_{10}$;

R$_{12}$ and R$_{13}$ is H, (CH$_2$)nOH, (CH$_2$)nNH$_2$, (CH$_2$)nNR$_{10}$R$_{11}$, (CH$_2$)nOR$_{11}$, (CH$_2$)nF, (CH$_2$)nOC(O)R$_{11}$, (CH$_2$)nNHC(O)R$_{11}$, or X—W—Y;

m is 1 or 2;

n is 0–4;

p is 0 or 1;

X is O, S, CH$_2$, or NH;

W is a spacer group made up of a chain of 4 to 100 atoms, and optionally also comprising of substituted carbon and/or ntrogen atoms and optionally including oxygen or sulphur atoms;

Y is OH, SH, NH$_2$, CH=O, CH=CH$_2$, CO$_2$H, CONHNH$_2$, or NH-biotinyl, or a protected form of one of these end functionalities.

The lower alkyl groups contain 1 to about 8 carbon, and preferably 1 to about 3 carbon atoms, and can be straight, branched-chain or cyclic saturated aliphatic hydrocarbon groups.

Examples of suitable alkyl grops include methyl, ethyl and propyl. Examples of branched alkyl groups include isopropyl and t-butyl. Examples of suitable cyclic aliphatic groups typically contain 3–8 carbon atoms and include cyclopentyl and cyclohexyl. The aromatic or aryl groups are preferably pehnyl or alkyl substituted aromatic groups (aralkyl) such as phenyl C$_{1-3}$ alkyl such as benzyl.

Examples of substituted cycloalkyl groups include cyclic aliphatic groups typically containing 3–8 carbon atoms in the ring substituted with alkyl grops typically having 1–6 carbon atoms and/or hydroxy group. Usually 1 or 2 substituted groups are presented.

The esters are typically lower alkyl esters having 1 to about 12 carbon atoms and preferably 1 to about 3 carbon atoms and aryl esters containing 6 to 14 carbon atoms. The alkyl esters can be straight-chain, branched-chain or cyclic saturated aliphatic hydrocarbons.

Examples of some alkyl esters are methyl, ethyl, propyl, isopropyl, t-butyl, cyclopentyl and cyclohexyl esters. The aryl esters are preferably phenyl or alkyl substituted aromatic esters (alkaryl) including C$_{1-3}$ alkyl substituted phenyl such as benzyl.

The lower alkylene group can be straight, branched chain or cyclic unsaturated hydrocarbon grop and contains 2–8 carbon atoms and preferably 2–3 carbon atoms. Examples of alkylene grops are vinyl, 1-propenyl, allyl, isopropenyl, 2-methyl-2-propenyl and cyclopentenyl.

The N-heterocyclic rings contain 3–7 atoms in the ring. The heterocyclic rings can be substituted such as with a lower alkyl grop. Examples of suitable heterocyclic groups are pyrrolidino, methylpiperidino and 2-ethylpiperidino.

Suitable spacer groups W include, but are not limited to, linear peptides, oligosaccharides, polyols, polyethylene glycol groups, hydrocarbon groups and hydrocarbon groups linked together with oxygen or sulphur atoms or with carbonyl, amido, urea or hydrazide functionalities. Spacer groups W may also comprise combinations of these various groups.

Suitable protecting groups for the end functionality Y include, but are not limited to, esters of the OH, SH and CO$_2$H groups, carbamates of the NH$_2$ and CONHNH$_2$ groups, and acetals of the CH=O group.

As used herein, the term "hydrocarbon group" includes saturated and unsaturated straight or branched hydrocarbon groups, including aryl groups, and combinations of such groups.

Pharmaceutically acceptable salts of the compounds of formula (I) include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

The compounds of the present invention bind relatively strongly to influenza virus neuraminidase, with IC$_{50}$ of 10 $\mu$M or better.

Compounds of the present invention can be prepared by a variety of methods. By way of illustration purposes, synthesis of some of the preferred compounds is given below:

(I)

In the formula (I)

R$_2$=H;

R$_9$=CO$_2$H;

R$_4$=NH$_2$, or NHC(=NH)NH$_2$;

Z=CH—CH(NHCOCH$_3$)-1-ethyl-propyl;

U=CH;

P=0;

R$_{12}$=X—W—Y;

R$_{13}$=H;

X is OC(O)NH;

W is (CH$_2$)$_6$, (CH$_2$)$_6$NHCONH(CH$_2$)$_6$, (CH$_2$CH$_2$O)$_2$CH$_2$CH$_2$, (CH$_2$)$_6$(NHCOCH$_2$)$_3$, (CH$_2$)$_6$NHCO(CH$_2$)$_{11}$, (CH$_2$)$_6$NHCO(CH$_2$)$_5$, (CH$_2$)$_6$[NHCO(CH$_2$)$_5$]$_4$, (CH$_2$)$_6$[NHCO(CH$_2$)$_5$]NHCOCH$_2$(OCH$_2$CH$_2$)$_{16}$, (CH$_2$)$_6$[NHCO(CH$_2$)$_5$]$_2$, (CH$_2$)$_6$[NHCO(CH$_2$)$_5$]$_4$NH—COCH$_2$CH$_2$, or (CH$_2$)$_6$NHCOCH$_2$CH$_2$;

Y is NH$_2$, NH-Biotin, CONHNHBoc, NHBoc, CONHNH$_2$, or CO$_2$H.

Synthetic Scheme:

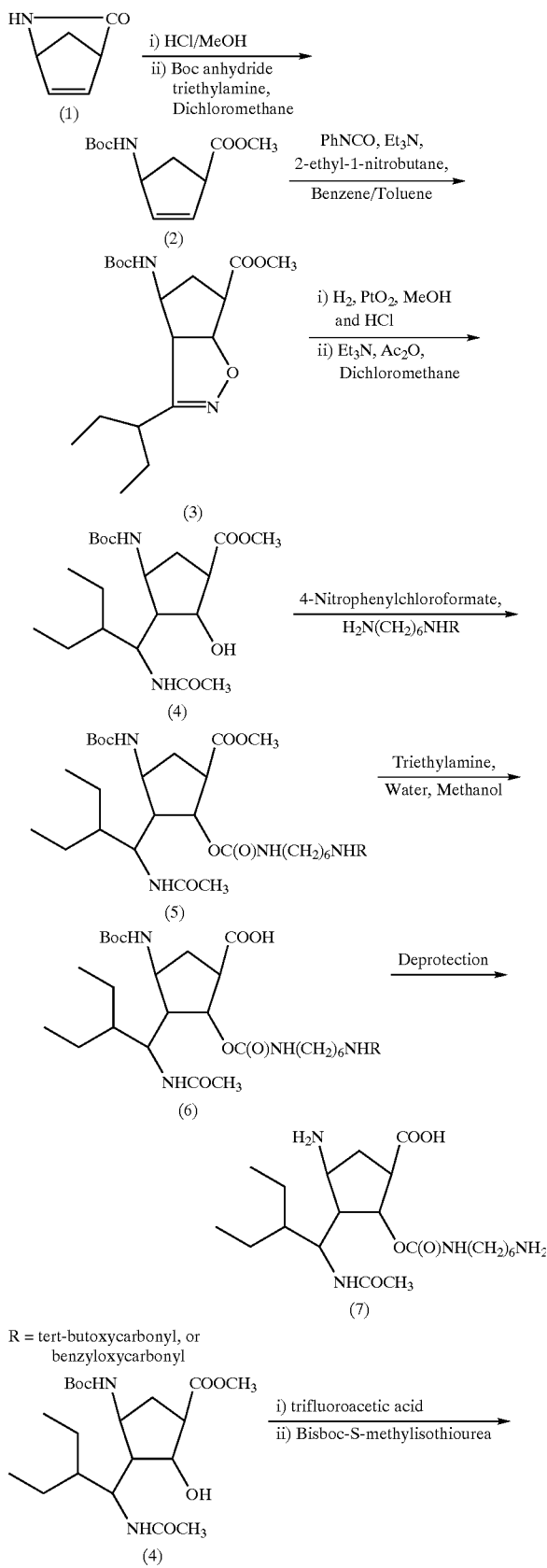

R = tert-butoxycarbonyl, or benzyloxycarbonyl

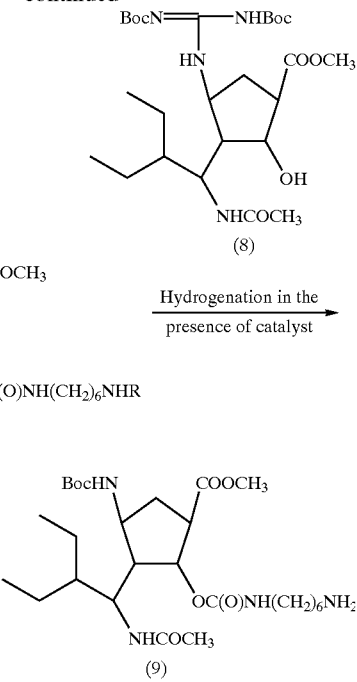

R = benzyloxycarbonyl

The following non-limiting examples are presented to further illustrate the present invention:

EXAMPLE 1

The compound wherein $R_{12}$=OC(O)NH(CH$_2$)$_6$NH$_2$ and $R_4$=NH$_2$ in structure I, with all other groups the same as mentioned above is prepared as follows:

The starting material, Lactam (1, −, + or racemic mixture) is heated at reflux temperature with methanolic HCl. The solvent is evaporated and the residue is washed with ether to give methyl 4-amino-2-cyclopenten-1-carboxylate hydrochloride, which is further reacted with di-tert-butyl dicarbonate and triethylamine to give methyl 4-tert-butoxycarbonylamino-2-cyclopenten-1-carboxylate (2). Compound (2) is reacted with 2-ethyl-1-nitrobutane/triethylamine and phenylisocyanate to give the cycloadduct (3). The desired isomer is separated and is hydrogenated in the presence of catalyst to give the corresponding amine, which is acetylated with acetic anhydride to give methyl 3-(1'-acetylamino-2'-ethyl)butyl-4-tert-botoxycarbonylamino-2-hydroxycyclopentane-1-carboxylate (4). Hydroxy compound (4) on reaction with 4-nitrophenyl chloroformate and amino protected 1,6-diaminohexane [H$_2$N(CH$_2$)$_6$NHR] gives the compound (5), which on ester hydrolysis with triethylamine in methanol/water gives (6). The deprotection of amino functionalities produces the target (7).

EXAMPLE 2

The compound wherein $R_{12}$=OC(O)NH(CH$_2$)$_6$NH$_2$ and $R_4$=NHC(=NH)NH$_2$ in structure I, with all other groups the same as mentioned above is prepared as follows:

compound (4) in Example 1 is hydrolyzed with trifluoroacetic acid to give corresponding amine, which on reaction with bis boc S-methyl isothiourea or boc protected pyrazole carboxamidine gives corresponding boc protected guanidino compound (8). Further reactions are the same as described in Example 1 to give the target compound.

EXAMPLE 3

The compound wherein $R_{12}$=OC(O)NH(CH$_2$CH$_2$O)$_2$CH$_2$CH$_2$NH$_2$ and $R_4$=NH$_2$ in structure I, with all other groups the same as mentioned above is prepared as follows:

Compound (4) is reacted with H$_2$N(CH$_2$CH$_2$O)$_2$CH$_2$CH$_2$NHR in place of 1,6-diaminohexane derivative as given in Example 1. The hydrolysis of ester and deprotection of amino group gives the target compound.

EXAMPLE 4

The compound wherein $R_{12}$=OC(O)NH(CH$_2$)$_6$NH-Biotin and $R_4$=NH, fin structure I, with all other groups the same as mentioned above is prepared as follows:

Compound (5), when R=benzyloxycarbonyl, is hydrogenated in the presence of a catalyst to give (9). Amine (9) is reacted with N-hydroxysuccinimide ester of biotin to give the corresponding compound with —OC(O)NH(CH$_2$)$_6$NH-Biotin side chain. The hydrolysis of ester and deprotection of amino group gives the target compound.

EXAMPLE 5

The compound wherein $R_{12}$=OC(O)NH(CH$_2$)$_6$(NHCOCH$_2$)$_3$NH-Biotin and $R_4$=NH$_2$ in structure I, with all other groups the same as mentioned above is prepared as follows:

Compound (5), when R=benzyloxycarbonyl, is hydrogenated in the presence of a catalyst to give (9). Amine (9) is reacted with 6-Biotinylaminotriglycine and isobutyl chloroformate in the presence of triethylamine and N-methylmorpholine to give the corresponding compound with —OC(O)NH(CH$_2$)$_6$(NHCOCH$_2$)$_3$NH-Biotin side chain. The hydrolysis of ester and deprotection of amino group gives the target compound.

EXAMPLE 6

The compound wherein $R_{12}$=OC(O)NH(CH$_2$)$_6$NHCO(CH$_2$)$_{11}$NH-Biotin and $R_4$=NH$_2$ in structure I, with all other groups the same as mentioned above is prepared as follows:

Compound (5), when R=benzyloxycarbonyl, is hydrogenated in the presence of a catalyst to give (9). Amine (9) is reacted with Biotinylaminodacanoic acid and carbonyldiimidazole to give the corresponding compound with —OC(O)NH(CH$_2$)$_6$NHCO(CH$_2$)$_{11}$NH-Biotin side chain. The hydrolysis of ester and deprotection of amino group gives the target compound.

EXAMPLE 7

The compound wherein $R_{12}$=OC(O)NH(CH$_2$)$_6$NHCO(CH$_2$)$_5$—NH-Biotin and $R_4$=NH$_2$ in structure I, with all other groups the same as mentioned above is prepared as follows:

Compound (5), when R=benzyloxycarbonyl, is hydrogenated in the presence of a catalyst to give (9). Amine (9) is reacted with Biotinylaminodacanoic acid and carbonyldiimidazole to give the corresponding compound with —OC(O)NH(CH$_2$)$_6$NHCO(CH$_2$)$_5$—NH-Biotin side chain. The hydrolysis of ester and deprotection of amino group gives the target compound.

EXAMPLE 8

The compound wherein $R_{12}$=OC(O)NH(CH$_2$)$_6$[NHCO(CH$_2$)$_5$]$_4$NH$_2$ and $R_4$=NH$_2$ in structure I, with all other groups the same as mentioned above is prepared as follows:

Compound (5), when R=benzyloxycarbonyl, is hydrogenated in the presence of a catalyst to give (9). Amine (9) is reacted with 6-[6'-(6"-tert-butoxycarbonylaminocaproyl)-diaminocaproyl]-aminocaproic acid and isobutyl chloroformate in the presence of pot-tert-butoxide and N-methylmorpholine to give the corresponding compound with —OC(O)NH(CH$_2$)$_6$[NHCO(CH$_2$)$_5$]$_4$NHBoc side chain. The hydrolysis of ester and deprotection of amino group gives the target compound.

EXAMPLE 9

The compound wherein $R_{12}$=OC(O)NH(CH$_2$)$_6$[NHCO(CH$_2$)$_5$]$_4$NH-Biotin and $R_4$=NH$_2$ in structure I, with all other groups the same as mentioned above is prepared as follows:

Compound (5), when R=benzyloxycarbonyl, is hydrogenated in the presence of a catalyst to give (9). Amine (9) is reacted with 6-[6'-6"-benzyloxycarbonylaminocaproyl)-diaminocaproyl]-aminocaproic acid and isobutyl chloroformate in the presence of pot-tert-butoxide and N-methylmorpholine to give the corresponding compound with —OC(O)NH(CH$_2$)$_6$[NHCO(CH$_2$)$_5$]$_4$NHCbz (Cbz=benzyloxycarbonyl) side chain. Hydrogenolysis and further reaction with Biotin N-hydroxysuccinimide ester gives the compound with OC(O)NH(CH$_2$)$_6$[NHCO(CH$_2$)$_5$]$_4$NH-Biotin side chain. The hydrolysis of ester and deprotection of amino group gives the target compound.

EXAMPLE 10

The compound wherein $R_{12}$=OC(O)NH(CH$_2$)$_6$[NHCO(CH$_2$)$_5$]$_4$NHC(O)CH$_2$CH$_2$C(O)NHNH$_2$ and $R_4$=NH$_2$ in structure I, with all other groups the same as mentioned above is prepared as follows:

Compound (5), when R=benzyloxycarbonyl, is hydrogenated in the presence of a catalyst to give (9). Amine (9) is reacted with 6-{6'-[6"(N-tert-butoxycarbonylhydrazidosuccinyl)aminocaproyl]-diaminocaproyl}-aminocaproic acid and isobutyl chloroformate in the presence of pot-tertbutoxide and N-methylmorpholine to give the corresponding compound with OC(O)NH(CH$_2$)$_6$[NHCO(CH$_2$)$_5$]$_4$—NHC(O)CH$_2$CH$_2$C(O)NHNHBoc side chain. The hydrolysis of ester and deprotection of amino groups gives the target compound.

EXAMPLE 11

The compound wherein $R_{12}$=OC(O)NH(CH$_2$)$_6$NHCOCH$_2$CH$_2$CO$_2$H and $R_4$=NH$_2$ in structure I, with all other groups the same as mentioned above is prepared as follows:

compound (5), when R=benzyloxycarbonyl, is hydrogenated in the presence of a catalyst to give (9). Amine (9) is reacted with succinic anhydride to give the corresponding compound with OC(O)NH(CH$_2$)NHCOCH$_2$CH$_2$CO$_2$H side chain. The hydrolysis of ester and deprotection of amino group gives the target compound.

All compounds with $R_4$-guanidino group are prepared the same way as described in Examples from 3 to 11, starting from compound (8) instead of compound (4).

The method of the present invention for detecting influenza virus is applicable to all known strains of influenza A and influenza B.

Preferably, the compound of the present invention is linked via a spacer group to a surface or to a detectable label. The spacer group should be sufficiently long that the detectable label is exposed on the surface of the virus particle.

The method of the present invention may use selective capture and concentration of the virus, followed by detection of the virus using any convenient conventional method; the detection method need not have inherent selectivity. For example, the compound of the present invention may be attached to a support material, such as a membrane or polymer, such that virus particles will be selectively captured and concentrated when a sample is passed over or through the support. Therefore in one embodiment of the invention, the spacer group terminates in a functionality able to bind to a surface. Many suitable functionalities are known in the art. For example, the terminal functionality may be a biotinyl group which can be used to attach the binder to a surface coated with avidin, streptavidin, or an antibody directed against biotin.

Alternatively, the terminal functionality may for example be an amino group which can be used to conjugate the neuraminidase binder to a carboxy-comprising surface.

Alternatively, a selective detection approach may be used; the virus particles in a sample may for example be exposed to a compound of the invention coupled to a detectable label, under conditions such that the compound binds selectively to the viral neuraminidase on the surface of the viral particle. The detectable label can be covalently coupled to the compound of the present invention. The detectable label is then detected using any convenient method. For some detection systems, it is convenient to focus the sample into a confined area, for example a spot or a line on a surface. This may be achieved by a variety of methods; for example, the sample may be suspended or non-selectively captured onto a filter or other support material, and then exposed to the labelled compound of the invention as described above. There are several known methods for the non-selective capture of the influenza virus, for example on a fetuin-coated surface (*J. Virological Methods*, 1992, 39: 111) or on a suitable membrane (*J. Virological Methods*, 1992, 40: 77). Another suitable detection system could be an optical assay device as described by Miller, B. J. et al, U.S. Pat. No. 5,418,136.

The compound of the present invention can be attached to a support, for example as a narrow band across a length of porous membrane. The test sample can then be applied at the other end of the membrane and allowed to flow across the band or bound compound. Any influenza virus particles in the test sample will be trapped by the membrane-bound compound and thus retained in the narrow band. In the second stage of the test, a detectable label attached to the neuraminidase binder is allowed to flow through the membrane across the band of bound influenza virus particles. The presence of influenza virus is then shown by an observable change in the membrane at the site of the bound compound. Suitable chromatographic assay devices have been described, for example by Chandler, H. M., International Patent Application No. WO 92/21977.

A very large number of suitable detection systems are known in the art, for example biotin-streptavidin, enzymic systems, such as horseradish peroxidase or alkaline phosphatase, fluorescence systems, chemiluminescence systems, colloidal gold, radioactive labels and agglutination systems. It is contemplated that colloidal gold linked to a neuraminidase binder via a spacer group will be a particularly convenient detectable label. Another convenient detection system would utilize a compound of the present invention covalently coupled to horseradish peroxidase. The skilled person will readily be able to select a suitable detection system and to optimize conditions for detection, without undue experimentation.

Suitable types of clinical samples for use in the method of the invention include throat swabs, nasal swabs, nasopharyngeal washings, nasal washes and gargles, or combinations of any of these; the gargles may optionally be concentrated, for example by ultracentrifugation, if necessary, but it is expected that this will only be the case when the number of viral particles is low.

It will be clearly understood that the label which is linked to the spacer group may be an epitope suitable for use in antibody detection kits, such as those described in U.S. Pat. No. 4,943,522 by Eisinger et al (assigned to Quidel); in optical assay devices having an active receptive surface, such as those described in U.S. Pat. No. 5,418,136 by Miller et al (assigned to Biostar, Inc.); or in agglutination detection systems such as those described in U.S. Pat. No. 4,894,347 and International Patent Application No. WO 91/04492. It is also contemplated that biosensor systems are suitable for use in the method of the invention. For example, a carbohydrate biosensor surface for detection of bacteria has been described (Nilsson, K. G. I. and C. F. Mandenius, *BioTechnology*, 1994, 12: 1376–1378).

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound selected from the group represented by the following formula:

$$\begin{array}{c} (R_{12})p \\ | \\ Z \diagup U \diagdown \diagup R_9 \\ \phantom{Z} \phantom{U} \diagdown R_1 \\ R_4 \phantom{xxx} R_{13} \end{array}$$

wherein:

U is CH;

Z is —CH—CH($R_3$)n$R_2$;

$R_1$ is H;

$R_9$ is $(CH_2)nCO_2H$, $(CH_2)nSO_3H$, $(CH_2)nPO_3H_2$, $(CH_2)nNO_2$, esters thereof, or salts thereof;

$R_2$ is NHC(O)$R_5$, NHC(S)$R_5$, or NHSO$_2R_5$;

$R_3$ is H, $(CH_2)nCO_2R_{10}$, $(CH_2)mOR_{10}$, C(O)N($R_{10}$)m, $(CH_2)nN(R_{10})m$, CH($R_{10})m$, $(CH_2)n(R_{10})m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, C(=N$R_{10}$)N($R_{10}$)m, NHR$_{10}$, NHC(=N$R_{10}$)N($R_{10}$)m, $(CH_2)$m-X—W—Y, $CH_2CH(X—W—Y)CH_2OR_{10}$, $CH(X—W—Y)CH(OR_{10})CH_2OR_{10}$, CH(X—W—Y)

$CH_2(OR_{10})$, $CH(OR_{10})CH(X—W—Y)CH_2OR_{10}$, $CH(OR_{10})CH_2(X—W—Y)$, $CH_2CH(X—W—Y)CH_2NHR_{10}$, $CH(X—W—Y)CH(OR_{10})CH_2NHR_{10}$, $CH(X—W—Y)CH_2(NHR_{10})$, $CH(OR_{10})CH(X—W—Y)CH_2NHR_{10}$, or $CH(NHR_{10})CH_2(X—W—Y)$;

$R_4$ is $(CH_2)nOH$, $(CH_2)nNR_{10}R_{11}$, $(CH_2)nNH_2$, $(CH_2)nC(=NH)(NH_2)$, $(CH_2)nNHC(=NR_{11})NH_2$, $(CH_2)nNHC(=NR_7)NH_2$, $(CH_2)nCN$, $(CH_2)nN_3$, $C(=NH)NH_2$, $C(NR_7)NH_2$, or $C(NR_{11})NH_2$;

$R_5$ is H, lower alkyl, branched chain alkyl, cyclic alkyl, halogen substituted alkyl, aryl, substituted aryl, or $CF_3$;

$R_7$ is H, $(CH_2)nOH$, $(CH_2)nCN$, $(CH_2)nNH_2$, or $(CH_2)nNO_2$;

$R_{10}$ is H, lower alkyl, lower alkylene, branched alkyl, cyclic alkyl, $(CH_2)n$ aromatic, $(CH_2)n$ substituted aromatic, or when m is 2 both $R_{10}$ groups can also be interconnected to form an N substituted heterocyclic ring, or other 5 or 6 membered heterocyclic ring;

$R_{11}$ is lower alkyl, branched alkyl, $(CH_2)m$ aromatic, or $C(O)OR_{10}$;

$R_{12}$ is $(CH_2)nOH$, $(CH_2)nNH_2$, $(CH_2)nNR_{10}R_{11}$, $(CH_2)nOR_{11}$, $(CH_2)nF$, $(CH_2)nOC(O)R_{11}$, $(CH_2)nNHC(O)R_{11}$, or X—W—Y;

$R_{13}$ is H or $R_{12}$;

m is 1 or 2;

n is 0–4;

p is 1;

X is O, S, $CH_2$, or NH;

W is a spacer group made up of a chain of 4 to 100 atoms, and optionally also comprising of substituted carbon and/or nitrogen atoms and optionally including oxygen or sulphur atoms;

Y is OH, SH, $NH_2$, CH=O, CH=$CH_2$, $CO_2H$, $CONHNH_2$, or NH-biotinyl, or a protected form of one of these end functionalities.

2. A method of detecting influenza virus, comprising the step of exposing a sample suspected to comprise influenza virus to at least one compound according to claim 1, wherein the at least one compound is capable of binding specifically to the active site of influenza virus neuraminidase.

3. The method of claim 2 wherein the at least one compound is attached to a support material such that virus particles will be selectively captured and concentrated when a sample is passed over or through the support.

4. The method of claim 2 wherein the at least one compound is linked via a spacer group to a surface.

5. The method of claim 4 wherein the spacer group terminates in a functionality able to bind to a surface.

6. The method of claim 5 wherein the terminal functionality is a biotinyl group and the surface is coated with avidin, streptavidin, or an antibody directed against biotin.

7. The method of claim 5 wherein the terminal functionality is an amino group and the surface comprises carboxy groups.

8. The method of claim 2 wherein the at least one compound is linked to a detectable label.

9. The method of claim 8 wherein the detectable label is covalently coupled to-the at least one compound.

10. The method of claim 8 wherein the virus particles in a sample are exposed to the at least one compound coupled to a detectable label, under conditions such that the at least one compound binds selectively to the viral neuraminidase on the surface of the viral particle.

11. The method of claim 8 which comprises the steps of selective capture and[]concentration of the virus.

12. The method of claim 2 comprising the step of selective capture and selective detection of influenza virus.

13. The method of claim 12 comprising the steps of:
a) exposing the sample to a neuraminidase binder bound to a support, and
b) exposing influenza virus particles retained on the support to the at least one compound.

14. The method of claim 2 in which the at least one compound has an $IC_{50}$ for binding of less than 10 μM.

15. The compound of claim 1 represented by the formula:

$$\text{(I)}$$

[structure with $(R_{12})_p$, U, Z, $R_9$, $R_1$, $R_4$, $R_{13}$]

$R_1$=H;

$R_9$=$CO_2H$;

$R_4$=$NH_2$, or NHC(=NH)$NH_2$;

Z=CH—CH(NHCOCH$_3$)-1-ethyl-propyl;

U=CH;

P=1:

$R_{12}$=X—W—Y;

W=A—B;

X is O;

A is —C(O)NH;

B is $(CH_2)_6$, $(CH_2)_6NHCONH(CH_2)_6$, $(CH_2CH_2O)_2CH_2CH_2$, $(CH_2)_6(NHCOCH_2)_3$, $(CH_2)_6NHCO(CH_2)_{11}$, $(CH_2)_6NHCO(CH_2)_6[NHCO(CH_2)_5]_4$, $(CH_2)_6[NHCO(CH_2)_5]NHCOCH_2(OCH_2CH_2)_{16}$, $(CH_2)_6[NHCO(CH_2)_5]_2$, $(CH_2)_6[NHCO(CH_2)_5]_4NH—COCH_2CH_2$, or $(CH_2)_6NHCOCH_2CH_2$;

Y is $NH_2$, NH-Biotin, CONHNHBoc, NHBoc, $CONHNH_2$, or $CO_2H$.

16. The compound of claim 2 wherein $R_{12}$ is OC(O)NH$(CH_2)_6NH_2$ and $R_4$ is $NH_2$.

17. The compound of claim 2 wherein $R_2$ is OC(O)NH$(CH_2)_6NH_2$ and $R_4$ is NHC(=NH)$NH_2$.

18. The compound of claim 2 wherein $R_{12}$ is OC(O)NH$(COH_2CH_2O)_2CH_2H_2NH_2$ and $R_4$ is $NH_2$.

19. The compound of claim 2 wherein $R_{12}$ is OC(O)NH$(CH_2)_6$NH-Biotin and $R_4$ is $NH_2$.

20. The compound of claim 2 wherein $R_{12}$ is OC(O)NH$(CH_2)_6(NHCOCH_2)_3$NH-Biotin and $R_4$ is $NH_2$.

21. The compound of claim 2 wherein $R_{12}$ is OC(O)NH$(CH_2)_6NHCO(CH_2)_{11}$NH-Biotin and $R_4$ is $NH_2$.

22. The compound of claim 2 wherein $R_{12}$ is OC(O)NH$(CH_2)_6NHCO(CH_2)_5$—NH-Biotin and $R_4$ is $NH_2$.

23. The compound of claim 2 wherein $R_{12}$ is OC(O)NH$(CH_2)_6[NHCO(CH_2)_5]_4NH_2$ and $R_4$ is $NH_2$.

24. The compound of claim 2 wherein $R_{12}$ is OC(O)NH$(CH_2)_6[NHCO(CH_2)_5]_4$NH-Biotin and $R_4$ is $NH_2$.

25. The compound of claim 2 wherein $R_{12}$ is OC(O)NH$(CH_2)_6[NHCO(CH_2)_5]_4NHC(O)CH_2CH_2C(O)NHNH_2$ and $R_4$ is $NH_2$.

26. The compound of claim 2 wherein $R_{12}$ is OC(O)NH$(CH_2)_6NHCOCH_2CH_2CO_2H$ and $R_4$ is $NH_2$.

27. A method of detecting influenza virus, comprising the step of exposing a sample suspected to comprise influenza virus to at least one compound according to claim 15, wherein the at least one compound is capable of binding specifically to the active site of influenza virus neuraminidase.

28. The method of claim 15 wherein the at least one compound is attached to a support material such that virus particles will be selectively captured and concentrated when a sample is passed over or through the support.

29. The method of claim 28 wherein the at least one compound is linked via a spacer group to a surface.

30. The method of claim 29 wherein the spacer group terminates in a functionality able to bind to a surface.

31. The method of claim 30 wherein the terminal functionality is a biotinyl group and the surface is coated with avidin, streptavidin, or an antibody directed against biotin.

32. The method of claim 30 wherein the terminal functionality is an amino group and the surface comprises carboxy groups.

33. The method of claim 15 wherein the at least one compound is linked to a detectable label.

34. The method of claim 33 wherein the detectable label is covalently coupled to the at least one compound.

35. The method of claim 33 wherein the virus particles in a sample are exposed to the at least one compound coupled to a detectable label, under conditions such that the at least one compound binds selectively to the viral neuraminidase on the surface of the viral particle.

36. The method of claim 33 which comprises the steps of selective capture and concentration of the virus.

37. The method of claim 15 comprising the step of selective capture and selective detection of influenza virus.

38. The method of claim 37 comprising the steps of:
a) exposing the sample to a neuraminidase binder bound to a support, and
b) exposing influenza virus particles retained on the support to the at least one compound.

39. The method of claim 15 in which the at least one compound has an $IC_{50}$ for binding of less than 10 $\mu$M.

* * * * *